US006284531B1

United States Patent
Zhu et al.

(10) Patent No.: US 6,284,531 B1
(45) Date of Patent: Sep. 4, 2001

(54) MULTI-COMPARTMENT DEVICE FOR CULTIVATING MICROORGANISMS

(76) Inventors: Hong Zhu; Hongwei Liu, both of 1650 Tasco Close, Victoria (CA), V8N 5P2

( * ) Notice: Subject to any disclaimer, the term of this patent is extended or adjusted under 35 U.S.C. 154(b) by 0 days.

(21) Appl. No.: 09/481,605

(22) Filed: Jan. 12, 2000

(51) Int. Cl.[7] .................................................. C12M 1/20
(52) U.S. Cl. .................................. 435/305.3; 435/297.5; 435/288.5; 435/287.7
(58) Field of Search .......................... 435/287.6, 287.7, 435/287.8, 288.2, 288.3, 288.4, 288.5, 297.1, 297.5, 304.2, 305.2, 305.3, 809

(56) References Cited

U.S. PATENT DOCUMENTS

| | | |
|---|---|---|
| 2,124,250 * | 7/1938 | Hoag . |
| 2,761,813 * | 9/1956 | Goetz . |
| 3,301,769 * | 1/1967 | Steel . |
| 3,562,114 * | 2/1971 | Steidl et al. . |
| 3,769,936 | 11/1973 | Swanson . |
| 3,960,658 | 6/1976 | Avakian . |
| 4,012,288 | 3/1977 | Lyman . |
| 4,118,280 * | 10/1978 | Charles et al. . |
| 4,308,351 * | 12/1981 | Leighton et al. . |
| 4,311,477 | 1/1982 | Kitamura . |
| 4,503,150 | 3/1985 | Triolo . |
| 4,565,783 | 1/1986 | Hansen . |
| 4,587,018 * | 5/1986 | Blomback et al. . |
| 4,689,301 | 8/1987 | Adet . |
| 4,878,312 | 11/1989 | Shimizu . |
| 4,977,702 | 12/1990 | Fortin . |
| 5,089,413 | 2/1992 | Nelson . |
| 5,225,164 | 7/1993 | Astle . |
| 5,232,838 | 8/1993 | Nelson . |
| 5,659,997 | 8/1997 | Sprehe . |
| 5,662,576 | 9/1997 | Sprehe . |
| 5,693,537 | 12/1997 | Wilson . |
| 5,714,384 | 2/1998 | Wilson . |
| 5,817,510 | 10/1998 | Pandey . |
| 5,869,321 | 2/1999 | Franklin . |
| 5,932,460 * | 8/1999 | Mills et al. . |
| 5,952,191 | 9/1999 | Morozov . |
| 5,976,780 * | 11/1999 | Shah . |
| 6,066,496 * | 5/2000 | Bridges . |

FOREIGN PATENT DOCUMENTS

| | | |
|---|---|---|
| 1055169 | 5/1979 | (CA) . |
| 2006181B | 5/1982 | (GB) . |

* cited by examiner

Primary Examiner—William H. Beisner

(57) ABSTRACT

A laboratory device is disclosed for growing microorganisms in a multi-compartment format, which provides convenience for dispensing, inoculation, incubation and harvesting when it is used for liquid cultures. The device includes a solid frame having formed within it a plurality of culturing compartments defined by solid side-walls built in the frame and plastic film and an assembly comprising an absorbing substrate and two non-absorbing fiber pads in each of the culturing compartments. These elements are generally rectangular in shape and the device can be sized to stack for incubation and storage. An access port and a series of apertures on the frame arranged a specific configuration permit introduction of liquid such as a liquid growth medium or a sample suspension into the culturing compartments simultaneously and equally. The use of the absorbing substrate, fiber pads and plastic film arranged in a specific assembly greatly increases the surface area and air transfer in the culturing compartments and thereby allows microorganisms to grow in liquid culture without agitation. The liquid cultures can be harvested easily by retrieving the absorbing substrate from the device.

18 Claims, 5 Drawing Sheets

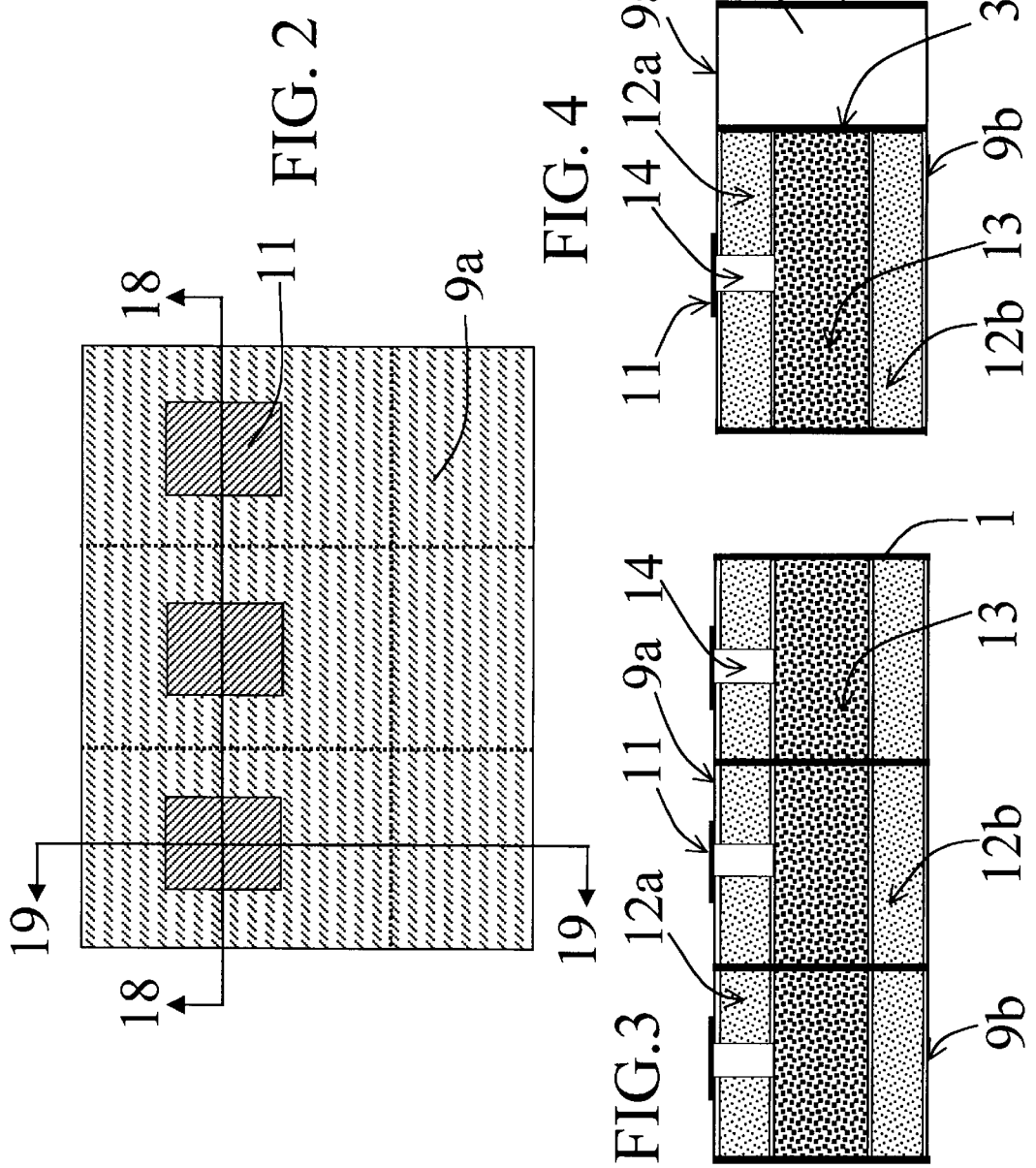

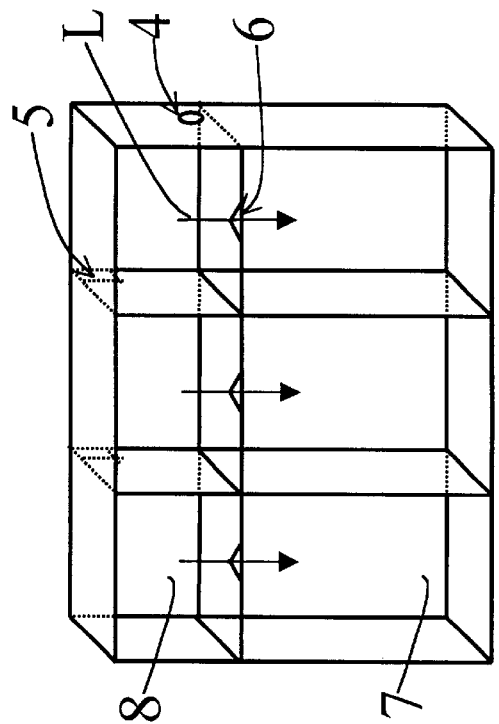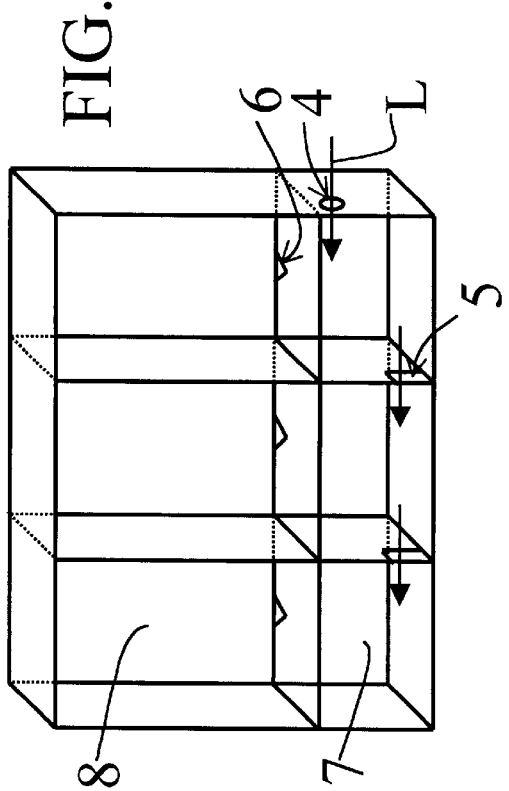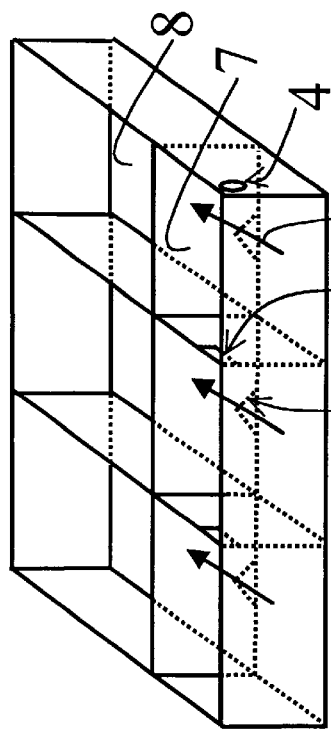
FIG. 5A
FIG. 5B
FIG. 5C

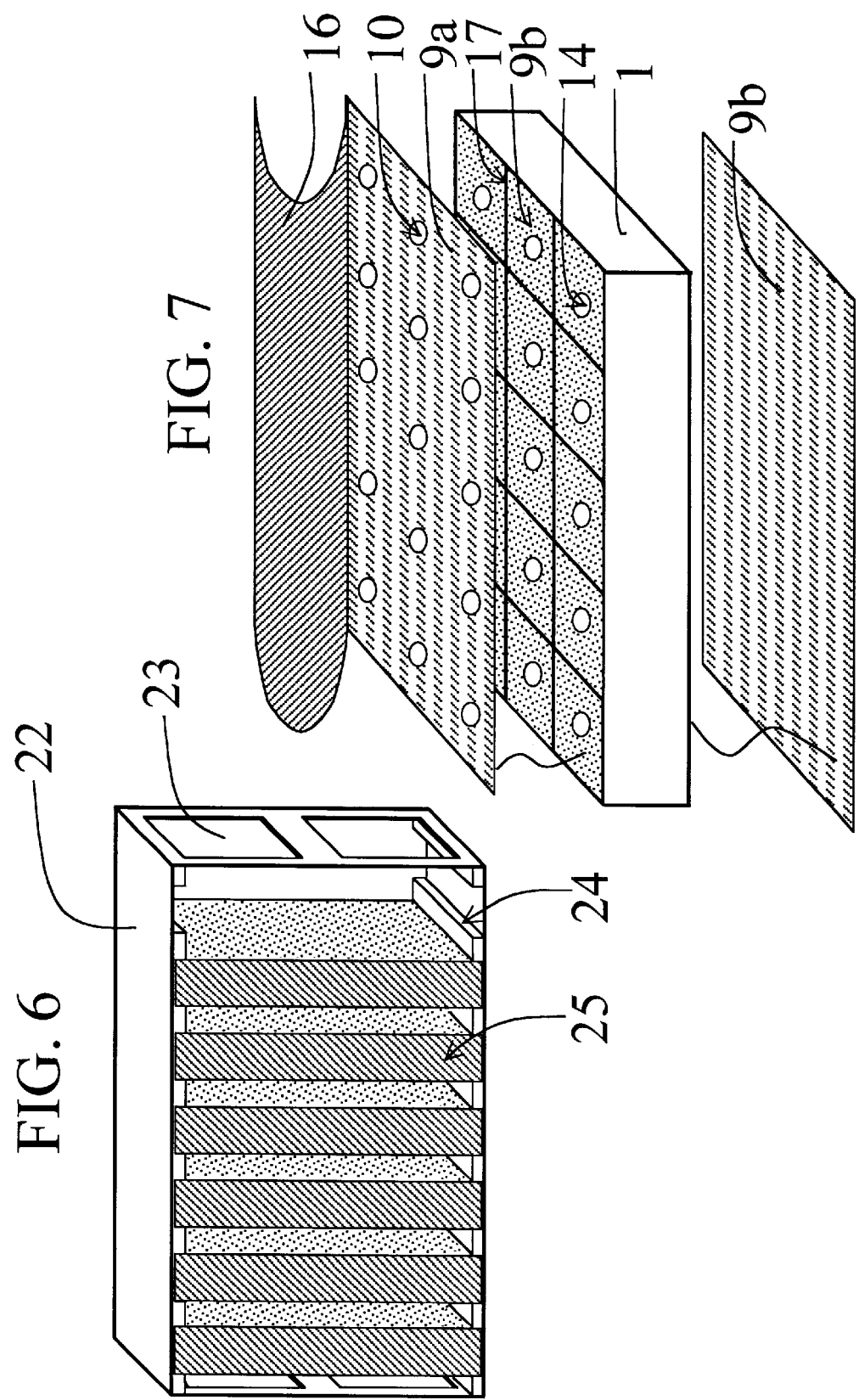

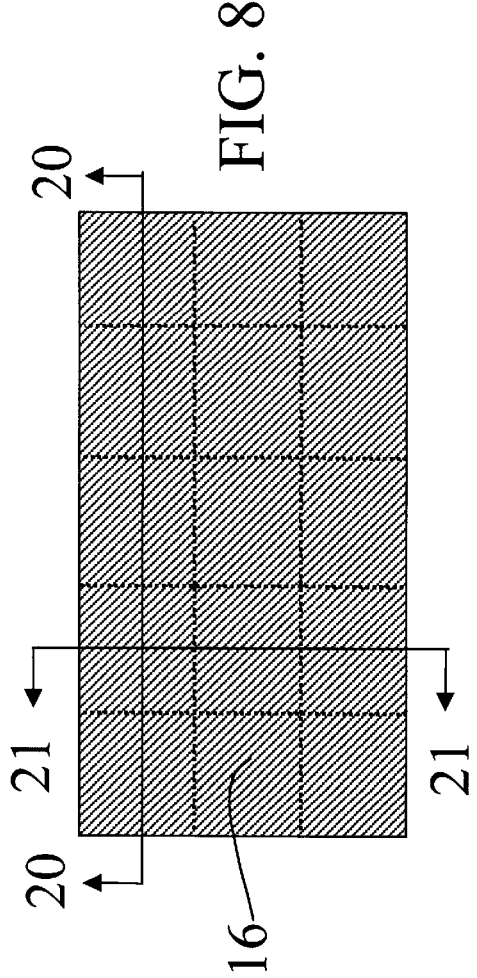
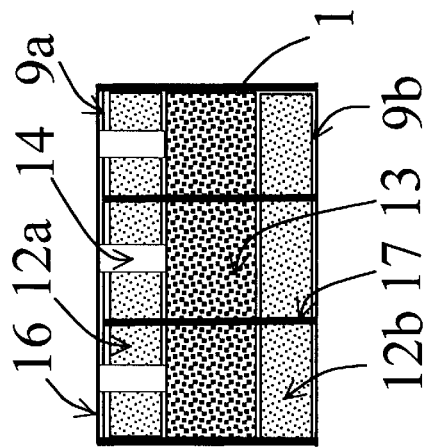
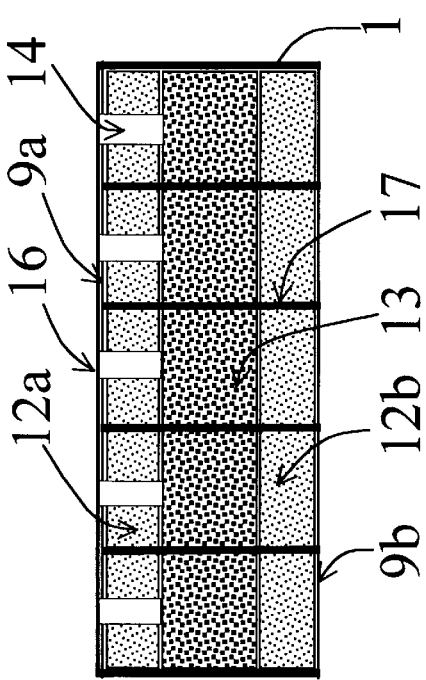

MULTI-COMPARTMENT DEVICE FOR CULTIVATING MICROORGANISMS

CROSS-REFERENCE TO RELATED APPLICATION

Not Applicable.

BACKGROUND OF THE INVENTION

1. Field of the Invention

The present invention relates generally to a laboratory device for growing microorganisms in liquid cultures in a multi-compartment format, which provides convenience for dispensing, inoculation, incubation and harvesting.

2. Prior Art

Simultaneous cultivation of a large number of microorganisms in laboratory conditions is common practice in microbiology for exploration of useful microbial activities and products. Conventionally, shake flasks, test tubes and petri dishes are used as the culturing devices. When these conventional devices are used, a separate unit must be used for each microorganism in each growth medium and each unit has to be handled individually throughout the culturing process. In a typical culturing process involving the conventional devices, such as shake flasks for example, a technician must dispense growth medium into each flask, sterilize the medium in flasks by autoclaving, inoculate each flask with a test sample, incubate the flasks on a mechanical shaker and harvest the liquid cultures for testing. This conventional culturing process is tedious, labor intensive and time consuming, particularly when it involves a large number of microorganisms, and it is often the bottleneck in the process of exploration of microorganisms in many microbiology laboratories.

To date, the prior art has provided several devices useful for culturing microorganisms, which simplify some steps of the conventional culturing process. Typically, multi-compartment devices are found to be easier and quicker to use than the conventional single compartment devices. For example, U.S. Pat. No. 3,960,658 discloses a multi-medium petri dish that comprises a petri-type dish where the base is divided into separate compartments for containing different culture media. Similarly, U.S. Pat. No. 4,012,288 describes a tissue culture cluster dish having a removable lid and a base with multi-wells formed therein. Each of the wells in the cluster dish can be used for one medium or one sample, and therefore, multi-wells in a single cluster dish can be used to host several media or samples at the same time. These multi-compartment cluster devices significantly reduce the need of handling each of individual petri dishes.

A problem associated with the use of such cluster devices is the greater chance of contamination of the device from outside environments when lids are removed for dispensing liquid media and inoculation. One approach to the problem is seen in U.S. Pat. No. 5,817,510 that discloses a cluster dish with a lid having a plurality of channels radiated from a central positioned aperture. Each of the channels extends through the lid to be positioned above each well in the base. Through the channels, liquid media and target microorganisms can be introduced into each of the wells without removing the lid, thereby reducing the chance of contamination. U.S. Pat. No. 3,769,936 discloses a petri dish cover with an orifice that may be opened or closed for dispensing media and inoculation without removing the lid. This approach is adapted to cluster devices as seen in U.S. Pat. No. 5,817,510. Although the lids with access orifices for cluster dishes are useful to reduce contamination during liquid communication, they do not provide any easiness or convenience for dispensing and inoculation because each well in a cluster device must be accessed individually. In no such cluster device or system in prior art, does it appear that all the wells can be accessed simultaneously and equally for the purpose of liquid communication.

A common feature of the multi-well cluster devices disclosed in prior art is that the lid and the base are constructed so that when in place on the base, a gap is created between the lid and the base. This feature not only permits air exchange between the inside and the outside of the devices, but also exposes all the wells to the same internal atmosphere. The feature, however, becomes a problem when liquid cultures are used because of possible cross contamination between the wells. Such cross contamination can occur as a result of the transfer of condensed moisture on the inner surface of the lid cover from one well to any other well or as a result of spills during handling. U.S. Pat. No. 4,012,288 discloses the use of circular ridge on the lower surface of the lid over the top of each well. The circular ridge on the lid can reduce the cross contamination caused by condensed moisture, but it does not prevent spills.

Another concern in using these open-lid cluster devices is safety. Because the gap allows air movement between the inside and the outside of the device without filtering, air-dispersible microorganisms (e.g. Aspergillus species produce air-dispersible spores) grown inside these devices can easily escape from these devices to contaminate the outside environment. Contamination is a primary concern in the practice of industrial exploration of microbial products from nature, which often involves cultivation of unknown microorganisms collected from diverse environments.

Several methods are known in prior art that may be used to provide a sealed environment for culturing microorganisms. One of them is the use of air-permeable plastic film. An example of such use is the bags made from air permeable plastic film for cultivating eatable mushrooms as described in U.S. Pat. Nos. 4,311,477, 4,878,312, 4,977,702, 5,662,576 and 5,659,997. In analogous fashion, air-permeable plastic film has been used in thin film culture plates for laboratory applications as disclosed in U.S. Pat. Nos. 4,565,783, 5,089,413, 5,232,838 and 5,869,321. A typical thin film culture plate comprises a waterproof substrate as the base coated with a gelling and a transparent, air-permeable cover film adhered to the upper surface of the gelling medium. Upon inoculation of the thin film plates, microorganisms will grow on the surface of the gelling medium under the air-permeable cover film. Other culturing devices involve airpermeable plastic film are disclosed in U.S. Pat. Nos. 5,693,537 and 5,714,384.

Most of microorganisms encountered in microbiology practice are aerobic microorganisms that often grow exclusively on the surface of the culture medium that exposes to air. For example, when cultured in petri dishes, most of microorganisms grow on the upper surface of the medium that faces the lid rather than on the lower surface that is in contact with the base of the petri dish. Similarly, the multi-compartment cluster devices known in prior art are designed for culturing microorganisms on a single surface of the medium. A disadvantage of such design is the relatively small area, often less than 50%, of the internal surface of the compartments being used for growth. With the conventional flasks and test tubes, microbiologists often use rotary shakers to increase the surface area and oxygen transfer for growth. The existing multi-compartment cluster devices, however, are unsuitable for use on shakers because of spills and cross contamination between compartments. Therefore, the surface area available for growth in multi-compartment cluster devices is restricted to the physical size of the compartments. In addition, the culturing methods involving shakers are not suitable for microorganisms that require a solid surface to attach and grow on.

One method to increase the surface area between air and liquid medium known in prior art is the use of highly porous plastic substrates such as sponges or foams. A good example of the effective use of such method is in biological digestion of nutrients in wastewater treatment as disclosed in British Pat. No. 2,006,181B and in Canadian Pat. No. 1,055,169. A typical plastic substrate suitable for culturing microorganisms is the flexible polyurethane foam described in U.S. Pat. Nos. 4,503,150 and 4,689,301 and in the report "Production of sulphated polysaccharides by a biophotoreactor having immobilized Porphridium cruentum cells" in Academie des Sciences, 1981, vol. 293, series III, pp. 35–37.

SUMMARY OF THE INVENTION

It is accordingly an object of the present invention to provide a multicompartment device in which liquid communication such as medium dispensing and inoculation to all the compartments can be performed simultaneously and equally.

It is another object of this invention to provide a multicompartment device in which cross contamination between compartments due to spills and condensation can be prevented.

It is a further object of this invention to provide a multi-compartment device in which microorganisms grow in a closed device to prevent air-dispersible microorganisms from contaminating the environment outside the device.

It is still further object of this invention to provide a multi-compartment device that has extended surface area for growth and for air transfer when it is used for liquid cultures.

It is yet another object of this invention to provide a multi-compartment device in which liquid cultures can be easily harvested and handled.

To attain the aforementioned objects, the present invention provides a multicompartment device comprising:

(a) a self-supporting frame having formed within it a plurality of openings defined by solid side-walls and dividers as receiving and culturing compartments which being sealed with plastic film at both the upper and lower surfaces, (b) an access port on said frame, which connects to each of said receiving and culturing compartments through apertures constructed in a specific configuration on said divider walls, and (c) an assembly consisting of a sponge-like, absorbing substrate and two coarse, non-absorbing fiber pads being inserted between said absorbing substrate and said plastic film in each of said culturing compartments.

In one embodiment, the present invention provides means for dispensing of a liquid material into said culturing compartments simultaneously and equally through said access port and said apertures in a specific configuration. This feature is particularly useful in the situation where the same liquid medium or sample needs to be dispensed into all culturing compartments within a cluster device. The feature eliminates the need for individually access of each culturing compartment in cluster devices seen in prior art which require more time and often encounters the problems of uneven-amount dispensing and of contamination from outside environment due to open-lid operation.

The present invention also provides means for access individual said culturing compartments for dispensing different media or samples into different said culturing compartments, comprising the step of injection of samples either through said plastic film by puncture or through an aperture constructed on said plastic film.

In an embodiment, the present invention provides means to prevent cross contamination between culturing compartment within the device by using said absorbing substrate to retain liquid cultures in said culturing compartments.

In another embodiment, the present invention provides means for growing microorganisms in a closed device to prevent air-dispersible microorganisms from contaminating the environment outside the device.

In a further embodiment, the present invention provides means to extend the air exchange surface for growth by the use of said absorbing substrate, said plastic film and said fiber pads in a specific assembly in said culturing compartment.

In yet another embodiment, the present invention provides an easy means for harvesting liquid cultures from said culturing compartments by simply removal of said absorbing substrate. The liquid cultures retained in said absorbing substrate can be handled, stored or processed as solid material rather than as liquid that requires more tedious handling.

These and other advantages and features of the present invention will be elucidated in, or be apparent from, the following description and the accompanying drawings.

BRIEF DESCRIPTION OF THE DRAWING

FIG. 2 is a top plan view of the device shown in FIG. 1.

FIG. 3 is a cross section view of the device shown in FIG. 2 along the line of 18—18.

FIG. 4 is a cross section view of the device shown in FIG. 2 along the line of 19—19.

FIGS. 5A, 5B, and 5C are perspective views illustrating basic concept for simultaneously dispensing liquid materials into the culturing compartments of the device.

FIG. 6 is a perspective view of the holding case for stacking the device.

FIG. 7 is an exploded perspective view of an alternative device using of the embodiments of the present invention.

FIG. 8 is a top plan view of the device shown in FIG. 7.

FIG. 9 is a cross section view of the device shown in FIG. 7 along the line of 20—20.

FIG. 10 is a cross section view of the device shown in FIG.7 along the line of 21—21.

DETAILED DESCRIPTION OF THE INVENTION

Figure 1:
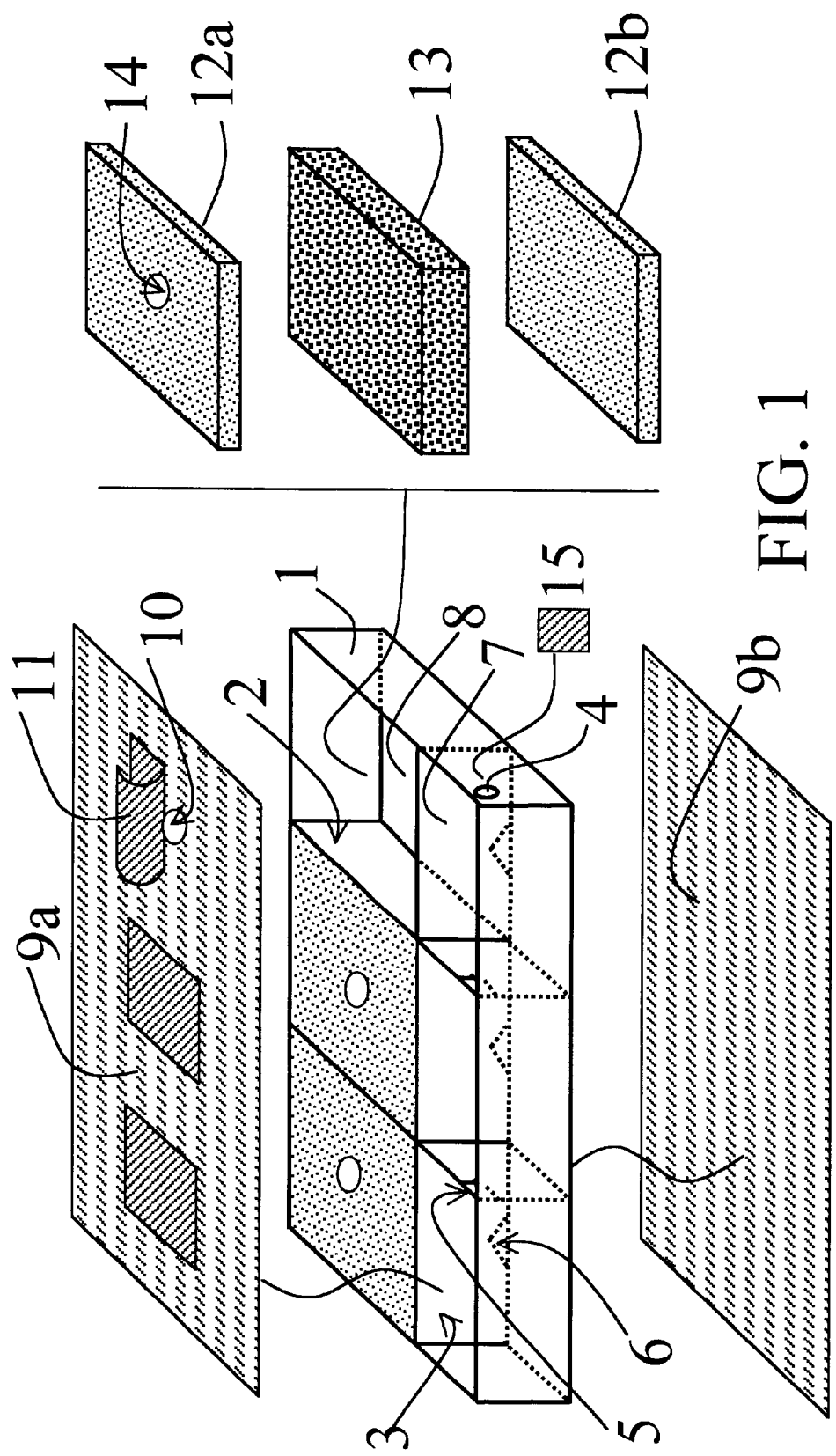
FIG. 1 is an exploded perspective view of the device of the present invention.

A preferred device of the present invention in the embodiment shown in FIGS. 1–4 is composed of a solid frame 1 with solid side-walls and dividers 2 and 3 to define the receiving compartments 7 and the culturing compartments 8. The upper and lower surfaces of each of the compartments 7 and 8 are sealed with plastic film 9a and 9b, respectively. A piece of porous, absorbing substrate 13 along with two pieces of coarse, non-absorbing, fiber pads 12a and 12b are placed in each of the culturing compartments 8 in a specific assembly as shown in FIG. 1.

Liquid communication is achieved between the exterior and interior of the device through the access port 4, between the receiving compartments 7 through apertures 5 and between the receiving compartments 7 and the culturing compartments 8 through apertures 6. The configuration of the positions of the access port 4 and apertures 5 and 6, as shown in FIG. 1 allows dispensing liquid materials such as liquid medium or sample into the culturing compartments 8 simultaneously (at the same time) and equally (with the same amounts). FIGS. 5A, 5B and 5C illustrate the basic concept of the simultaneous dispensing in operation. The liquid material L is delivered into the device through the access port 4 when the device is placed in the vertical position as shown in FIG. 5A with the receiving compartments 7 on the bottom. The liquid material L spreads evenly into the receiving compartments 7 through apertures 5 because of gravity flow. When a desired level of the liquid material L in each of the receiving compartments 7 is achieved as determined by users, the access port 4 is sealed with an non-venting material such as resilient tape 15. The device is then pushed backward down to the horizontal position as shown in FIG. 5B and immediately into an inverted vertical position as shown in FIG. 5C where the liquid material L flows into the culturing compartments 8 through apertures 6 and absorbed up by the substrate 13. It is important to note that the apertures 5 must be kept upward and above the liquid level when the device is turned into the positions as shown in FIG. 5B so that no unwanted liquid transfer occurs between the receiving compartments 7. When the liquid material L is absorbed into the substrate 13, the device can be handled, stored or incubated in any positions, though preferably in the position as shown in FIG. 5C.

As a feature aid to the users, the preferred device illustrated in FIGS. 1–4 has apertures 10 on the upper plastic film 9*a*. Users can use apertures 10 to access individual culturing compartments 8 for dispensing different media or samples or for taking samples from the culturing compartments 8. To facility these operations, channels 14 are constructed on the fiber pads 12*a* so that the absorbing substrate 13 can be reached and solid samples such as agar plugs can be directly placed on the absorbing substrate 13. The apertures 10 can be open or closed with the resilient tape strips 11 on the outer surface of the plastic film 9*a*. Alternatively, even without the construction of the access apertures 10, the plastic film 9*a* and 9*b* permits the entry through puncture and removal of a syringe or other instruments into the individual culturing compartments 8 and the entry points caused by the puncture can be sealed with resilient tapes.

In one embodiment of this invention, a porous, absorbing substrate 13 is used. The use of the absorbing substrate 13 is a great improvement in several aspects over existing multi-compartment cluster devices when liquid cultures are used. First, because it absorbs up and retains liquid, the absorbing substrate 13 prevents spills even if the device is inverted and thus prevents internal cross contamination between the culturing compartments 8. Secondly, because its porous structures the absorbing substrate 13 greatly extends the surface area for growth without increasing the physical size of the device. Thirdly, the use of the absorbing substrate 13 provides an easy means for harvesting liquid cultures from the culturing compartments 8 by simply removal of the absorbing substrate 13 out of the culturing compartments 8. The liquid cultures retained in the absorbing substrate 13 can be retrieved by pressing or squeezing the absorbing substrate 13 manually or mechanically. Alternatively, the liquid cultures along the absorbing substrate 13, without separating from the substrate 13, can be directly used in downstream processing such as extraction of secondary metabolites.

In another embodiment, non-absorbing fiber pads 12*a* and 12*b* are used. The use of fiber pads 12*a* and 12*b* creates air spaces between the absorbing substrate 13 and the plastic film 9*a* and 9*b* so that air transfer between the plastic film and the absorbing substrate 13 is greatly enhanced and the microorganisms can grow on both upper and lower surfaces of the absorbing substrate 13. The use of fiber pads 12*a* and 12*b* also reduce condensation formed on the inner surfaces of the plastic film 9*a* and 9*b*, because the pads 12*a* and 12*b* have numerous contact points with the films 9*a* and 9*b* which reduce the surface tension of water layer formed due to condensation. It is also contemplated that the pad 12*b* be used to retain dry medium that can be reconstituted upon in contact liquid material introduced into the culturing compartments 8 when the device is in the position as shown in FIG. 5B.

The use of plastic film 9*a* and 9*b* as shown in FIGS. 1–4 provides a completely sealed device for culturing microorganisms. Because the plastic film 9*a* and 9*b* are permeable to air but not to microorganisms and aqueous liquid, this invention prevents spills and the release of air-dispersible microorganisms to the outside environment. This safety consideration highlights the suitability of the present invention for use with microorganisms that are easily aerosolized and permits novices to work with microorganisms with reduced chance of contamination, as compared to other multicompartment cluster devices.

The use of the absorbing substrate 13, fiber pads 12*a* and 12*b* and plastic film 9*a* and 9*b* in the assembly as shown in FIGS. 1 greatly improves air transfer throughout the culturing compartments 8 over other multi-compartment devices in prior art. The use of the assembly allows adequate growth of microorganisms in liquid cultures under stationary incubation conditions without using shaker. In laboratory practice, the device can be stacked, as shown in FIG. 6, in a self-supporting holding case 22 having openings 23 on side-walls. The devices 25 are secured in the case 22 and spaced at approximately one inch apart from each other by the ribs 24.

Although the device shown in FIGS. 1–5 has three receiving compartments 7 and three culturing compartments 8, it is to be understood that within the scope of this present invention a greater or smaller number of the compartments or alternative designs using may be provided. FIGS. 7–10 illustrate an alternative construction of the device having a plurality of culturing-compartments defined by divider walls 17 built in the frame and the plastic film 9*a* and 9*b* and the assembly of the absorbing substrate 13 and fiber pads 12*a* and 12*b* shown in FIG. 1. Each of the culturing compartments is closed and separated from others by the dividing walls 17. The alternative device may be used for high sample throughput process in industrial laboratories, in which a large number of microorganisms and automatic equipment may be involved. In using the alternative device, the same or different liquid materials including growth media and test samples can be dispensed into the compartments 8 either manually or automatically by using multi-channel pettier through the apertures 10 on the plastic film 9*a*. The device is then sealed with the resilient tape 16, incubated and harvested as described for the device shown in FIG. 1.

In the embodiments of the present invention, the frame 1 with side-walls and dividers may be made of transparent or non-transparent plastic materials such as polyethylene, polypropylene, polycarbonate, polyurethane, or polyvinyl chloride. The plastic film 9a and 9b may be any plastic films or sheets that are permeable to air, particularly to oxygen and carbon dioxide, but not permeable to microorganisms and aqueous solutions. Suitable plastic film for use in this invention includes, but not limited to, those made of polyethylene, polypropylene or polyvinylidine fluoride. An example of these films includes Exxaire.™ breathable polylefin films manufactured by Exxon Chemical Co. The porous, adsorbing substrate 13 includes flexible, open-cell foams or sponges made of synthetic materials such as polyurethane and polyethylene. It is also contemplated that various porous, absorbing substrate materials with different surface properties be used in this invention to alter or induce growth and differentiation of microorganisms. The fiber pads 12a and 12b may be made from a wide range of non-absorbing absorbing synthetic or natural materials that allow air and aqueous solutions passing freely. An example of these pads suitable for this invention is the Scotch-Bite.™ No.98 scouring pads commercially available from 3M Company, St. Paul, Minn. The resilient tapes 11, 15 and 16 may be air-permeable or non-air permeable tapes made of synthetic materials. An example of these tapes is the 3M Micropore.™ tape manufactured by 3M company, St. Paul, Minn. Depending the materials used for construction the preferred embodiments, the device may sterilized by autoclaving or by gamma irradiation.

What is claimed is:

1. A multi-compartment device for culturing microorganisms comprising:
    (a) a self-supporting, solid frame having formed within it a plurality of openings defined by solid side-walls and dividers as receiving and culturing compartments which being sealed with plastic film on both the upper and lower surfaces,
    (b) an access port on a side-wall of the frame, which connects to each of said receiving and culturing compartments through apertures constructed in a specific configuration on the divider walls of the frame,
    (c) an assembly consisting of an absorbing substrate and two non-absorbing fiber pads being inserted between said absorbing substrate and said plastic film in each of said culturing compartments.

2. A device according to claim 1, wherein the positions of said access port and said apertures are arranged in a specific configuration to permit simultaneously and equally dispensing liquid materials into said culturing compartments.

3. A device according to claim 1, wherein there is a provided means for accessing individual said culturing compartments either through puncturing said plastic film or through an aperture constructed on said plastic film.

4. According claim 3, wherein there is a provided resilient tape strips to be used for sealing said aperture on said plastic film.

5. A device according to claim 1, wherein an assembly of said absorbing substrate, said non-absorbing pads and said plastic film is used to increase available surface area and to enhance air transfer throughout said culturing compartments for the growth of microorganisms in liquid cultures under the condition of stationary incubation.

6. According to claim 1, wherein the plastic film is an air-permeable film made of synthetic materials.

7. According to claim 1, wherein the absorbing substrate is a flexible, open cell, foam made of synthetic materials having capacity to absorb and retain liquid.

8. According to claim 1, wherein the non-absorbing pad is a fiber pad made of synthetic or natural materials that allow air and liquid passing freely.

9. According to claim 1, wherein there is a provided non-venting tape strip to be used for sealing said access port on the frame.

10. According to claims 1, wherein there is a provided channel constructed on said fiber pads to facility the access to said absorbing substrate for solid sample placement.

11. A multi-compartment device for culturing microorganisms comprising:
    (a) a self-supporting frame having formed within it a plurality of culturing compartments defined by solid side-walls and plastic film at both the upper and lower opening surfaces,
    (b) an aperture constructed on said plastic film on one side of the device, which connects to each culturing compartment,
    (c) an assembly consisting of an absorbing substrate and two non-absorbing fiber pads being inserted between said absorbing substrate and said plastic film in each of said culturing compartments.

12. A device according to claim 11, wherein there is a provided means for accessing individual said culturing compartments either through puncturing said plastic film or through an aperture constructed on said plastic film.

13. A device according to claim 11, wherein the assembly of said absorbing substrate, said non-absorbing pads and said plastic film is used to increase available surface area and air transfer for the growth of microorganisms in liquid culture in stationary incubation.

14. According to claim 11, wherein the plastic film is an air-permeable film made of synthetic materials.

15. According to claim 11, wherein the absorbing substrate is a flexible, open cell, foam made of synthetic materials having capacity to absorb and retain liquid.

16. According to claim 11, wherein the non-absorbing pad is a fiber pad made of synthetic or natural materials which allow air and liquid passing freely.

17. According to claim 11, wherein there is a provided air-permeable tape cover to be used for sealing said aperture on said plastic film.

18. According to claims 11, wherein there is a provided channel constructed on said pads to facility the access to said absorbing substrate.

* * * * *